(12) United States Patent
Kraus et al.

(10) Patent No.: US 6,193,675 B1
(45) Date of Patent: Feb. 27, 2001

(54) FLUID SAMPLING APPARATUS

(75) Inventors: Menachem Kraus, Rehovot; Eli Shemesh; Jacob Nijinski, both of Ashdod, all of (IL)

(73) Assignee: Teva Medical LTD, Ashdod (IL)

( * ) Notice: Subject to any disclaimer, the term of this patent is extended or adjusted under 35 U.S.C. 154(b) by 0 days.

(21) Appl. No.: 09/194,550

(22) PCT Filed: Feb. 27, 1997

(86) PCT No.: PCT/IL97/00074

§ 371 Date: Jan. 28, 1999

§ 102(e) Date: Jan. 28, 1999

(87) PCT Pub. No.: WO97/45714

PCT Pub. Date: Dec. 4, 1997

(30) Foreign Application Priority Data

May 30, 1996 (IL) ........................................................ 118497

(51) Int. Cl.$^7$ ............................................................ A61B 5/00
(52) U.S. Cl. ............................ 600/576; 600/573; 604/211
(58) Field of Search ................................... 600/573, 576, 600/577, 578, 583; 604/283, 411, 412, 413, 414, 905

(56) References Cited

U.S. PATENT DOCUMENTS

| | | | |
|---|---|---|---|
| 2,955,595 | * 10/1960 | Semple | 128/214 |
| 3,327,709 | * 6/1967 | Nehring et al. | 128/214 |
| 3,623,475 | 11/1971 | Sanz et al. | 128/2 R |
| 3,841,835 | 10/1974 | Kishimoto et al. | 23/253 R |
| 3,872,730 | 3/1975 | Ringrose et al. | 73/421 B |
| 3,877,465 | 4/1975 | Miyake | 128/2 F |
| 4,043,333 | * 8/1977 | Munsch | 128/214 R |
| 4,112,944 | * 9/1978 | Williams | 128/214 R |
| 4,266,543 | 5/1981 | Blum | 128/218 N |
| 4,580,564 | 4/1986 | Andersen | 128/314 |
| 4,759,756 | * 7/1988 | Forman et al. | 604/413 |
| 4,763,648 | 8/1988 | Wyatt | 128/673 |
| 4,774,964 | 10/1988 | Bonaldo | 128/763 |
| 4,790,827 | 12/1988 | Haber et al. | 604/198 |
| 4,843,017 | 6/1989 | Oberhardt et al. | 436/177 |
| 4,846,005 | 7/1989 | Bacehowski et al. | . |
| 4,869,249 | 9/1989 | Crossman et al. | 128/314 |
| 4,904,242 | * 2/1990 | Kulli | 604/110 |
| 4,920,970 | 5/1990 | Wyatt | 128/673 |
| 4,924,879 | 5/1990 | O'Brien | 128/770 |
| 4,934,015 | 6/1990 | Mink | 15/268 |

(List continued on next page.)

FOREIGN PATENT DOCUMENTS

| | | |
|---|---|---|
| 0428723 | 1/1996 | (EP) . |
| WO 93/21821 | 11/1993 | (WO) . |
| 96/21393 * | 7/1996 | (WO) .................................. 600/576 |

*Primary Examiner*—Max Hindenburg
*Assistant Examiner*—Charles Marmor, II
(74) *Attorney, Agent, or Firm*—Alston & Bird

(57) ABSTRACT

Apparatus for sampling fluid from a puncturable conduit, the apparatus including an elongate housing including a conduit puncturing portion and a clamp, the conduit puncturing portion being adapted to receive therein the puncturable conduit, a needle mount mounted in the elongate housing, a needle adapted for flow of fluid therethrough, the needle being fixedly mounted in the needle mount so as to have portions extending outward of the needle mount in opposite directions, a first end of the needle being pointed and protruding into, but not beyond, the conduit puncturing portion, such that the conduit puncturing portion substantially prevents inadvertent engagement of a user's finger with the first end of the needle, and wherein the clamp is operative to clamp the puncturable conduit in the conduit puncturing portion, thereby forcing the puncturable conduit towards the first end of the needle and causing the first end to puncture the puncturable conduit.

8 Claims, 5 Drawing Sheets

U.S. PATENT DOCUMENTS

| | | | |
|---|---|---|---|
| 4,981,140 | 1/1991 | Wyatt | 128/673 |
| 5,002,066 | 3/1991 | Simpson et al. | 128/760 |
| 5,014,718 | 5/1991 | Mitchen | 128/771 |
| 5,026,388 | 6/1991 | Ingalz | 606/182 |
| 5,084,034 | 1/1992 | Zanotti | 604/319 |
| 5,139,489 * | 8/1992 | Hollister | 604/192 |
| 5,286,453 | 2/1994 | Pope | 422/100 |
| 5,303,713 | 4/1994 | Kurose | 128/763 |
| 5,360,012 | 11/1994 | Ebara et al. | 128/764 |
| 5,377,756 | 1/1995 | Northrop et al. | 166/267 |
| 5,533,984 * | 7/1996 | Parmigiani | 604/263 |
| 5,620,008 * | 4/1997 | Shinar et al. | 128/764 |
| 5,928,166 * | 7/1999 | Shemesh et al. | 600/576 |

* cited by examiner

FLUID SAMPLING APPARATUS

FIELD OF THE INVENTION

The present invention relates to fluid sampling apparatus generally, and particularly to apparatus for sampling fluid from a puncturable conduit.

BACKGROUND OF THE INVENTION

Various types of apparatus for sampling fluids are known. In particular, various types of blood sampling apparatus are known in the art. The following patent documents are believed to represent the state of the art: U.S. Pat. Nos. 3,877,465; 4,763,648; 4,920,970; 4,934,015; 4,981,140; 5,002,066 & 5,084,034; European Patent Application 88906129.7 and PCT Published Patent Application WO 93/121821.

Often when blood is drawn from a donor and collected in a blood bag, it is desired to test samples of the blood before use thereof. In general, a plurality of tubing segments, which are sausage-like tubing pieces typically about 10 cm long, are attached to the blood bag. In blood bank laboratory tests, each segment is cut open with scissors and the contents are squeezed into a test tube. This can be a rather messy process.

SUMMARY OF THE INVENTION

The present invention seeks to provide improved and easy-to-use fluid sampling apparatus for use with puncturable conduits, which substantially overcomes the disadvantages of the prior art.

There is thus provided in accordance with a preferred embodiment of the present invention, apparatus for sampling fluid from a puncturable conduit, the apparatus including an elongate housing including a conduit puncturing portion and a clamp, the conduit puncturing portion being adapted to receive therein the puncturable conduit, a needle mount mounted in the elongate housing, a needle adapted for flow of fluid therethrough, the needle being fixedly mounted in the needle mount so as to have portions extending outward of the needle mount in opposite directions, a first end of the needle being pointed and protruding into, but not beyond, the conduit puncturing portion, such that the conduit puncturing portion substantially prevents inadvertent engagement of a user's finger with the first end of the needle, and a second end of the needle being in fluid communication with a fluid sampling tube, and wherein the clamp is operative to clamp the puncturable conduit in the conduit puncturing portion, thereby forcing the puncturable conduit towards the first end of the needle and causing the first end to puncture the puncturable conduit.

Additionally in accordance with a preferred embodiment of the present invention, the second end of the needle protrudes into, but not beyond, the elongate housing, such that the elongate housing substantially prevents inadvertent engagement of a user's finger with the second end of the needle.

Further in accordance with a preferred embodiment of the present invention, the conduit puncturing portion includes a conduit interface element which is substantially shaped complementarily to an outer periphery of the conduit.

The second end of the needle may be blunt. Alternatively, in accordance with another preferred embodiment of the present invention, the second end of the needle is pointed, and a puncturable resilient sheath is formed over the second end and onto at least a portion of the needle mount.

Additionally in accordance with a preferred embodiment of the present invention, the needle mount is removably mounted in the elongate housing.

Further in accordance with a preferred embodiment of the present invention, the needle is adhesively mounted in the needle mount.

BRIEF DESCRIPTION OF THE DRAWINGS

The present invention will be understood and appreciated more fully from the following detailed description, taken in conjunction with the drawings in which.

DETAILED DESCRIPTION OF A PREFERRED EMBODIMENT

Figure 1:
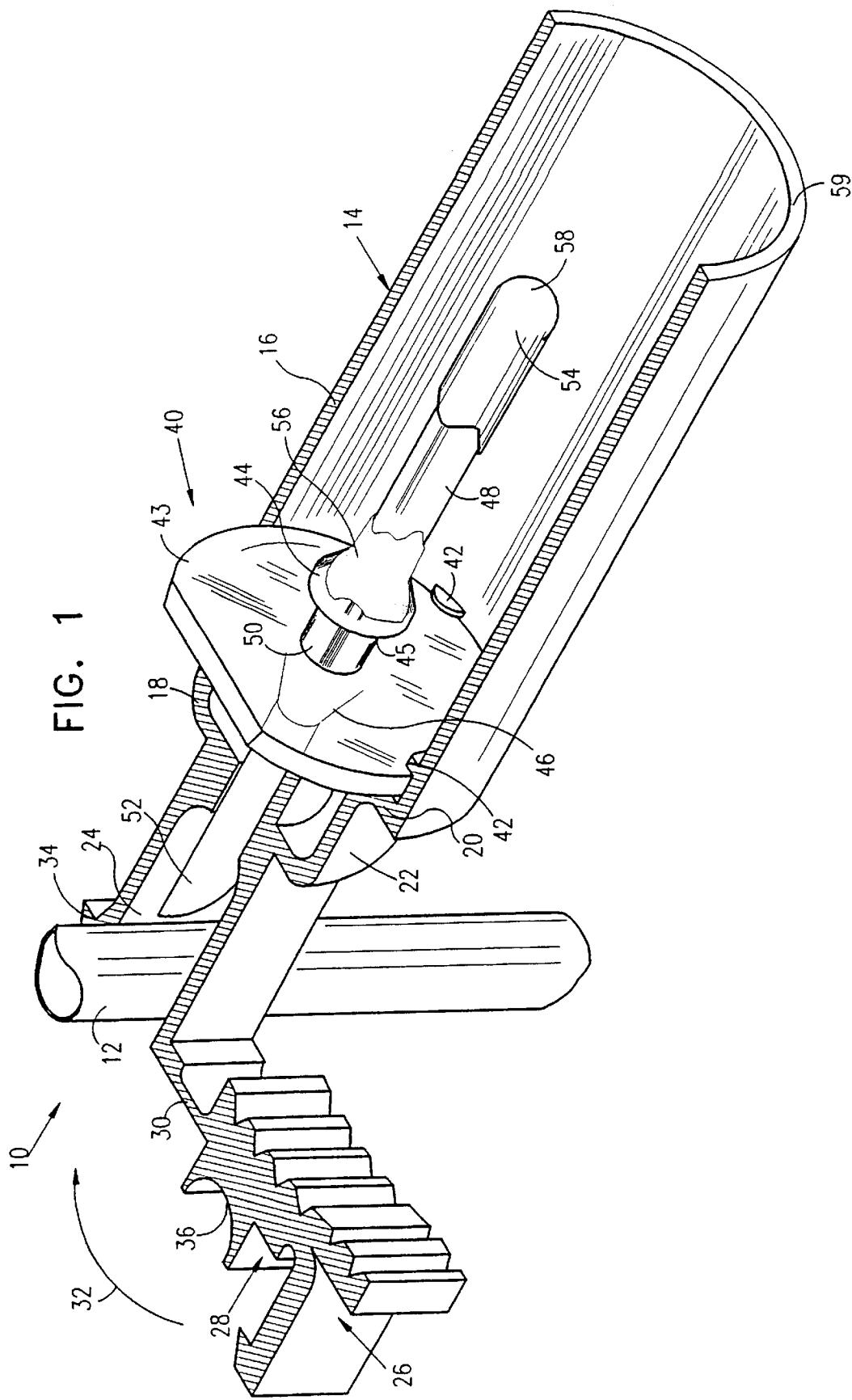
FIG. 1 is a simplified, cutaway pictorial illustration of apparatus for sampling fluid from a puncturable conduit, constructed and operative in accordance with a preferred embodiment of the present invention, the apparatus having a needle with two pointed ends.
Figure 2A:
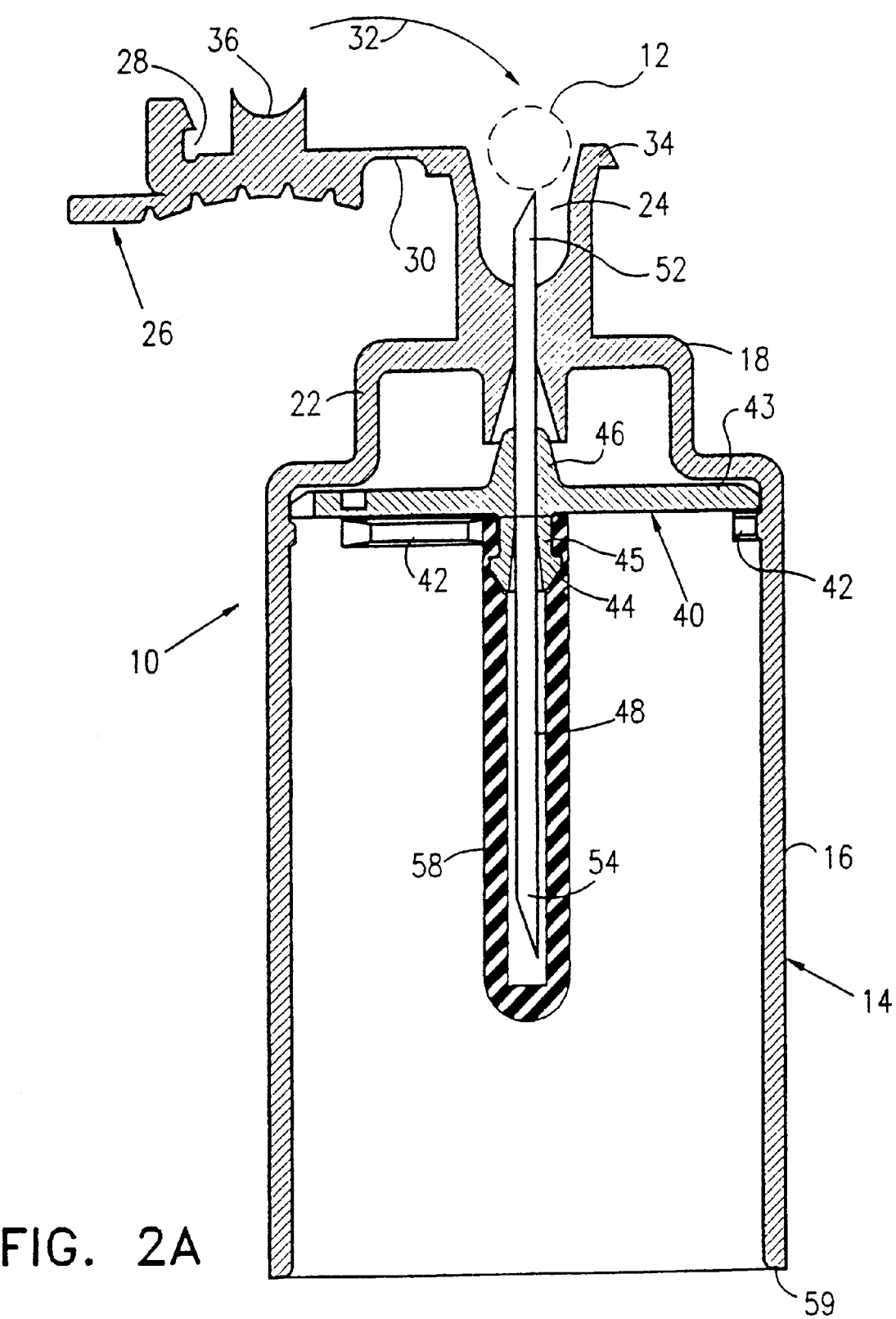
FIGS. 2A, 2B and 2C are simplified sectional illustrations of apparatus of FIG. 1, before and after puncturing a puncturable conduit, and after engagement with a sampling tube, respectively.

Reference is now made to FIGS. 1 and 2A which illustrate apparatus 10 for sampling fluid from a puncturable conduit 12, constructed and operative in accordance with a preferred embodiment of the present invention.

Apparatus 10 preferably includes an elongate housing 14, typically formed of plastic by injection molding. Housing 14 preferably comprises a generally circular cylindrical portion 16 and a neck portion 18 which are joined at a shoulder 20. Portion 16 is preferably longer and of larger radius than neck portion 18, portion 16 being intended for operative engagement with a sampling tube (not shown in FIGS. 1 and 2A).

Neck portion 18 is preferably cylindrical in shape at a base 22 thereof and terminates in an outwardly extending conduit puncturing portion 24. As seen in FIGS. 1 and 2A, conduit puncturing portion 24 is adapted to receive therein conduit 12. Preferably hingedly attached to conduit puncturing portion 24 is a clamp 26. Clamp 26 preferably has an engagement cutout portion 28 formed therein and includes a relatively thin pivoting portion 30. By folding clamp 26 in the direction of an arrow 32 about pivoting portion 30, a flange 34, preferably located at an extreme end of conduit puncturing portion 24, snappingly engages with engagement cutout portion 28, as will be described further hereinbelow. Clamp 26 preferably further includes a conduit interface element 36 which is substantially shaped complementarily to the outer periphery of conduit 12.

In accordance with a preferred embodiment of the invention there is provided a separately formed needle mount element 40, which is removably mounted in the elongate housing 14. Element 40 is seated against shoulder 20 and is retained thereagainst by a plurality of inwardly protruding retaining tabs 42.

Needle mount element 40 is preferably formed of plastic by injection molding and includes a planar portion 43 of a preferably truncated conical configuration, integrally formed with a pair of non-identical, hollow, male attachment portions 44 and 46, extending perpendicularly to planar portion 43 at the center of planar portion 43, which is apertured thereat. Preferably, male attachment portion 44 has an undercut 45.

Accordingly, planar portion 43 together with attachment portions 44 and 46 define an elongate channel through which extends a needle 48, having a roughened center section 50 and a first end 52 and a second end 54. Needle 48 is preferably hollow and adapted for flow of fluid therethrough.

Needle 48 is preferably fixedly frictionally and adhesively mounted in needle mount element 40 so as to have needle portions of differing lengths extending perpendicularly to planar portion 43 outward of the needle mount in opposite directions.

An adhesive 56, such as U. V. adhesive, is preferably disposed about an outward edge of attachment portion 44 in such a manner so as to provide a smooth transition between the outer surface of needle 48 and the maximum diametrical dimension of attachment portion 44. This particular arrangement enables relatively easy sliding of the open end of a puncturable resilient sheath 58 over second end 54 into frictionally retained engagement with attachment member 44, as seen in FIGS. 1 and 2A. Preferably, the open end of sheath 58 engages undercut 45 formed in attachment portion 44, for enhanced retention thereon.

In the embodiment of FIGS. 1 and 2A, both first 52 and second 54 ends of needle 48 are pointed. It is seen that first end 52 of needle 48 protrudes into, but not beyond, conduit puncturing portion 24, such that conduit puncturing portion 24 substantially prevents inadvertent engagement of a user's finger with first end 52. Furthermore, it is seen that second end 54 of needle 48 protrudes into, but not beyond, an end 59 of elongate housing 14, such that elongate housing 14 substantially prevents inadvertent engagement of a user's finger with second end 54.

Figure 2B:
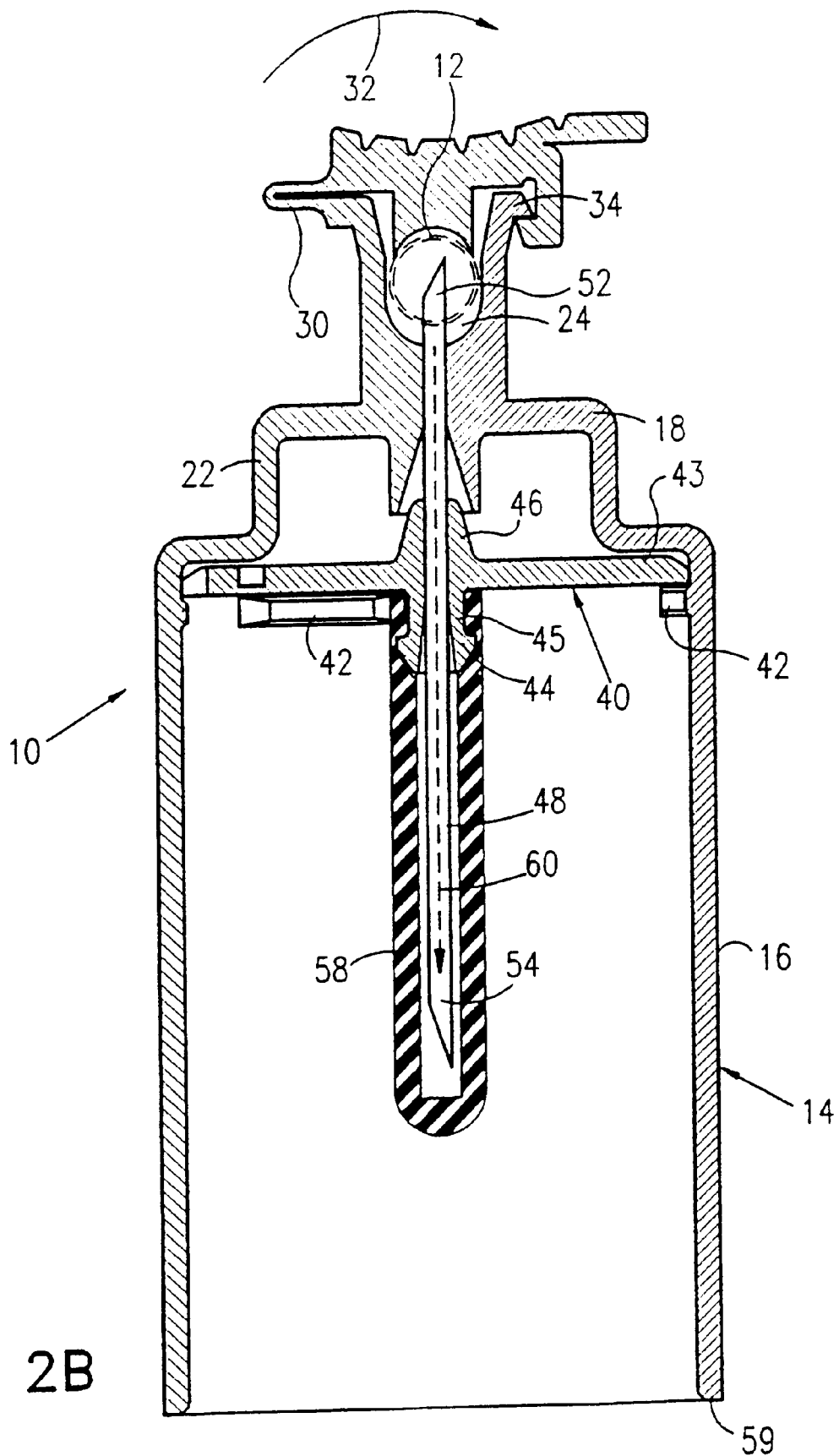
Figure 2C:
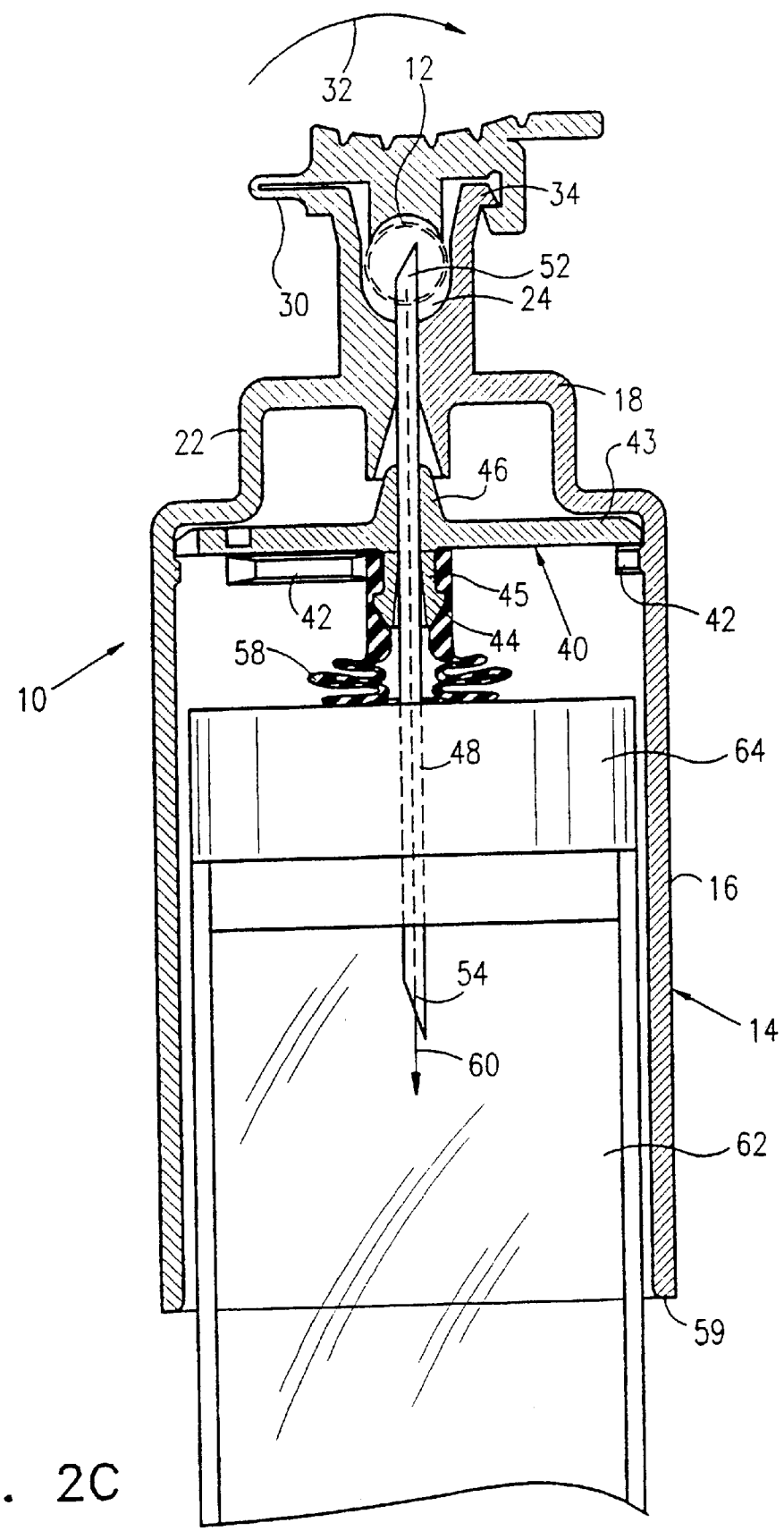

Reference is now additionally made to FIGS. 2B and 2C. As described hereinabove, FIG. 2A illustrates conduit 12 placed in conduit puncturing portion 24 and prior to puncturing thereof By folding clamp 26 about pivoting portion 30 in the direction of arrow 32, as seen in FIG. 2B, conduit interface element 36 forces conduit 12 towards pointed first end 52, thereby causing first end 52 to puncture conduit 12. A fluid 60, such as blood, then flows into needle 48. As seen in FIG. 2C, a sampling tube 62 may then be pushed onto second end 54 for collecting fluid 60 therein. Preferably sampling tube 62 is substantially hermetically sealed by a seal 64 which is punctured by second end 54 when engaging sampling tube 62 with needle 48.

Apparatus 10 may be particularly useful in applications such as, for example, donation of blood. In such a case, conduit 12 would be a blood donor tube attached to a blood donor, and apparatus 10 would be used to collect blood in sampling tube 62.

Figure 3:
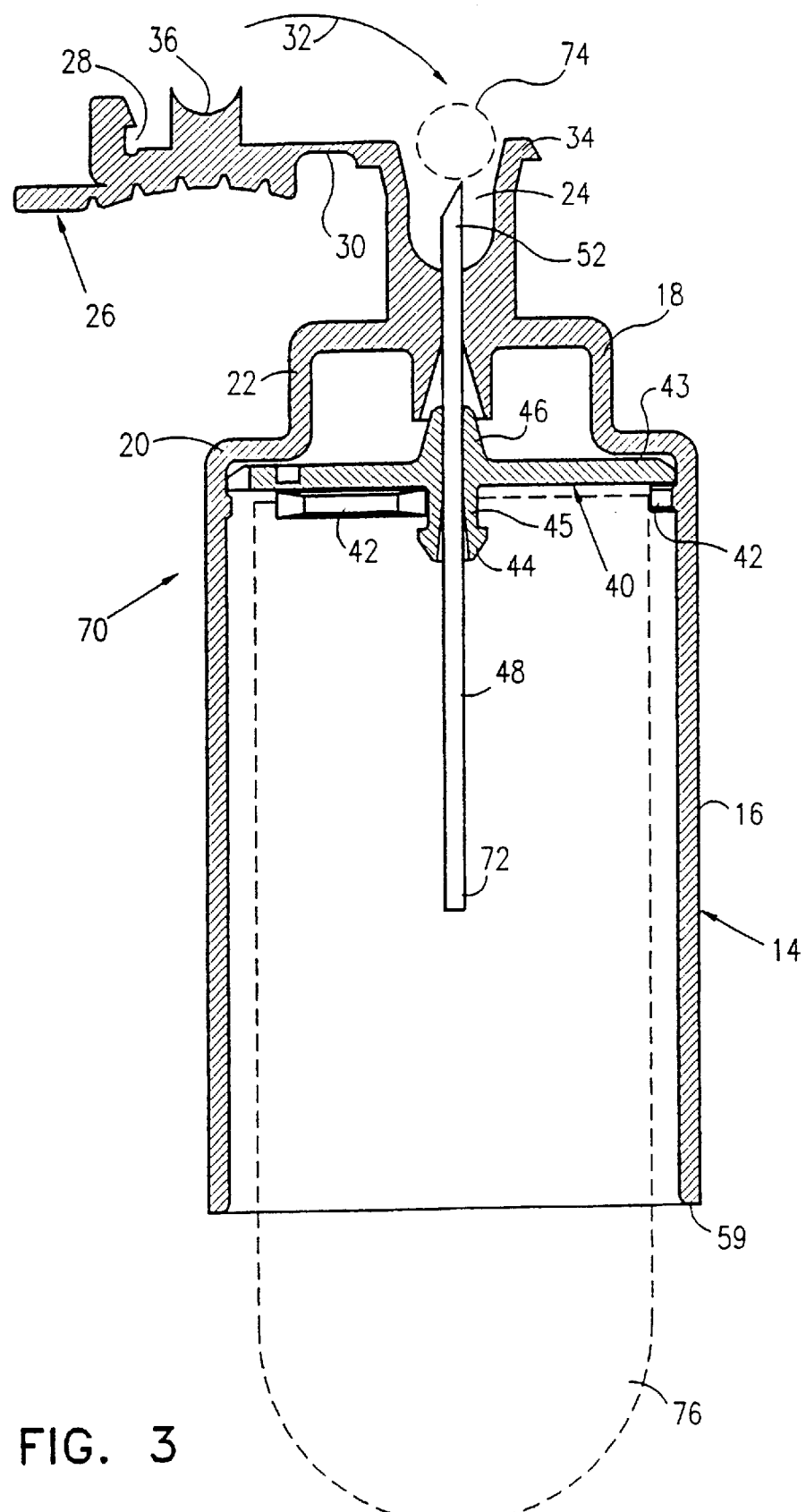
FIG. 3 is a simplified sectional illustration of apparatus for sampling fluid from a puncturable conduit, constructed and operative in accordance with another preferred embodiment of the present invention, the apparatus having a needle with only one pointed end.

Reference is now made to FIG. 3 which illustrates apparatus 70 for sampling fluid, constructed and operative in accordance with another preferred embodiment of the present invention. Apparatus 70 is preferably substantially identical with apparatus 10 described hereinabove, with like numerals designating like elements. Apparatus 70 differs from apparatus 10 in that a second end 72 of needle 48 is blunt and there is no sheath 58.

As seen in FIG. 3, a tubing segment 74 may be placed in conduit puncturing portion 24. Apparatus 70 is preferably held upright. Upon closing clamp 26 in the direction of arrow 32, segment 74 is punctured by first end 52 of needle 48. Segment 74 may then be manually squeezed to empty the contents of segment 74 into test tube 76 via second end 72.

Apparatus 70 may be particularly useful in applications such as, for example, examining blood in a blood bank laboratory. After having collected blood from a donor, and before infusing into a recipient, apparatus 70 may be used to empty blood which was collected in tubing segment 74 into test tube 76 for examination and matching.

It is appreciated that various features of the invention which are, for clarity, described in the contexts of separate embodiments may also be provided in combination in a single embodiment. Conversely, various features of the invention which are, for brevity, described in the context of a single embodiment may also be provided separately or in any suitable subcombination.

It will be appreciated by persons skilled in the art that the present invention is not limited by what has been particularly shown and described hereinabove. Rather the scope of the present invention is defined only by the claims which follow:

What is claimed is:

1. Apparatus for sampling fluid from a puncturable conduit, said apparatus comprising:

an elongate housing comprising a conduit puncturing portion, a clamp and a conduit interface element, said conduit puncturing portion being adapted to receive therein said puncturable conduit;

a needle mount mounted in said elongate housing;

a needle adapted for flow of fluid therethrough, said needle being fixedly mounted in said needle mount so as to have portions extending outward of said needle mount in opposite directions, a first end of said needle being pointed and protruding into, but not beyond, said conduit puncturing portion, such that said conduit puncturing portion substantially prevents inadvertent engagement of a user's finger with said first end of said needle; and wherein said clamp clamps said puncturable conduit in said conduit puncturing portion, said conduit interface element forces said puncturable conduit towards said first end of said needle and causes said first end to puncture said puncturable conduit.

2. Apparatus according to claim 1 and wherein said second end of said needle protrudes into, but not beyond, said elongate housing, such that said elongate housing substantially prevents inadvertent engagement of a user's finger with said second end of said needle.

3. Apparatus according to claim 1 and wherein said conduit interface element is substantially shaped complementarily to an outer periphery of said conduit.

4. Apparatus according to claim 1 and wherein said second end of said needle is blunt.

5. Apparatus according to claim 1 and wherein said second end of said needle is pointed, and a puncturable resilient sheath is formed over said second end and onto at least a portion of said needle mount.

6. Apparatus according to claim 1 and wherein said needle mount is removably mounted in said elongate housing.

7. Apparatus according to claim 1 and wherein said needle is adhesively mounted in said needle mount.

8. Apparatus for sampling fluid from a puncturable conduit, said apparatus comprising:

an elongate housing comprising a generally circular cylindrical portion and a neck portion which are joined at a shoulder, wherein said neck portion is generally cylindrical in shape at a base thereof and terminates in an outwardly extending conduit puncturing portion, said conduit puncturing portion being adapted to receive therein a conduit;

a needle mount mounted in said elongate housing;

a needle adapted for flow of fluid therethrough, said needle being fixedly mounted in said needle mount so as to have portions extending outward of said needle mount in opposite directions, a first end of said needle being pointed and protruding into, but not beyond, said conduit puncturing portion, such that said conduit puncturing portion substantially prevents inadvertent engagement of a user's finger with said first end of said needle; and a clamp hingedly attached to said conduit puncturing portion, said clamp having a conduit interface element and an engagement cutout portion formed therein and including a pivoting portion, wherein by folding said clamp about said pivoting portion, a flange located at an extreme end of said conduit puncturing portion snappingly engages with said engagement cutout portion, and said conduit interface element forces a conduit received in said conduit puncturing portion towards said first end, thereby causing said first end to puncture the conduit.

* * * * *

UNITED STATES PATENT AND TRADEMARK OFFICE
CERTIFICATE OF CORRECTION

PATENT NO. : 6,193,675 B1  Page 1 of 1
DATED : February 27, 2001
INVENTOR(S) : Kraus et al.

It is certified that error appears in the above-identified patent and that said Letters Patent is hereby corrected as shown below:

Title page,
Item [56] References Cited, FOREIGN PATENT DOCUMENTS,
Line 3, "96/21393" should read -- WO96/21393 --.

Item [74] *Attorney, Agent, or Firm,*
"Alston & Bird" should read -- Alston & Bird LLP --.

Column 1,
Line 15, "93/121821" should read -- 93/21821 --.

Column 4,
Line 35, after "wherein" insert -- when --;
Line 45, after "claim 1" cancel "and".

Signed and Sealed this

Sixth Day of November, 2001

Attest:

NICHOLAS P. GODICI
*Attesting Officer*  *Acting Director of the United States Patent and Trademark Office*